United States Patent
Frame et al.

(10) Patent No.: US 10,006,573 B2
(45) Date of Patent: Jun. 26, 2018

(54) CONNECTOR FOR MULTIPLE SIZED CONNECTIONS

(71) Applicant: Fisher & Paykel Healthcare Limited, Auckland (NZ)

(72) Inventors: Samuel Robertson Frame, Auckland (NZ); Martin Paul Friedrich Kramer, Auckland (NZ); Kevin Peter O'Donnell, Auckland (NZ); Graham Douglas Gourd, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 0 days. days.

(21) Appl. No.: 14/768,933

(22) PCT Filed: Feb. 20, 2014

(86) PCT No.: PCT/NZ2014/000020
§ 371 (c)(1),
(2) Date: Aug. 19, 2015

(87) PCT Pub. No.: WO2014/129912
PCT Pub. Date: Aug. 28, 2014

(65) Prior Publication Data
US 2016/0003393 A1 Jan. 7, 2016

Related U.S. Application Data

(60) Provisional application No. 61/767,209, filed on Feb. 20, 2013.

(51) Int. Cl.
*F16L 33/22* (2006.01)
*F16L 37/08* (2006.01)
(Continued)

(52) U.S. Cl.
CPC .......... *F16L 37/08* (2013.01); *A61M 16/0816* (2013.01); *F16L 33/22* (2013.01); *A61M 2039/1077* (2013.01); *F16L 2201/44* (2013.01)

(58) Field of Classification Search
CPC ....... A61M 16/0816; A61M 2039/1077; F16L 37/08; F16L 33/22
See application file for complete search history.

(56) References Cited

U.S. PATENT DOCUMENTS 3,768,476 A * 10/1973 Raitto ................... A61M 39/10
285/12
4,026,581 A * 5/1977 Pasbrig ............... F16L 37/0982
285/24
(Continued)

FOREIGN PATENT DOCUMENTS

| EP | 2407103 B1 | 11/2013 |
| GB | 2186652 A | 8/1987 |
| WO | WO 2008/058506 | 5/2008 |

OTHER PUBLICATIONS

International Search Report; PCT/NZ2014/000020; dated May 21, 2014; 3 pages.
Written Opinion; PCT/NZ2014/000020; dated May 21, 2014; 4 pages.

*Primary Examiner* — David E Bochna
(74) *Attorney, Agent, or Firm* — Knobbe, Martens, Olson & Bear, LLP

(57) ABSTRACT

A connector is used to connect a gases supply to a user. The user can be fitted with an interface, such as a cannula, while the gases supply can include a conduit. The connector interfaces between the conduit and the interface. The connector has a female assembly and a male assembly that connect together, such as by push fit. The male assembly includes an inner portion sized and configured to mate with a first female connector and an outer portion sized and (Continued)

configured to alternatively mate with a second female connector.

15 Claims, 6 Drawing Sheets

(51) Int. Cl.
*A61M 16/08* (2006.01)
*A61M 39/10* (2006.01)

(56) References Cited

U.S. PATENT DOCUMENTS

| | | | | |
|---|---|---|---|---|
| 4,030,494 A | * | 6/1977 | Tenczar | A61M 39/14 |
| | | | | 285/21.2 |
| 4,254,773 A | * | 3/1981 | Waldbillig | A61M 39/1055 |
| | | | | 285/281 |
| 4,369,781 A | * | 1/1983 | Gilson | A61M 5/346 |
| | | | | 285/332 |
| 4,538,836 A | * | 9/1985 | Krutten | A61M 39/10 |
| | | | | 285/24 |
| 5,062,420 A | * | 11/1991 | Levine | A61M 16/085 |
| | | | | 128/204.18 |
| 5,176,415 A | * | 1/1993 | Choksi | A61M 39/10 |
| | | | | 128/202.27 |
| 5,279,597 A | * | 1/1994 | Dassa | A61M 25/0111 |
| | | | | 285/339 |
| 6,273,087 B1 | * | 8/2001 | Boussignac | A61M 16/0858 |
| | | | | 128/200.12 |
| 6,484,724 B1 | * | 11/2002 | Sloan | A61M 16/085 |
| | | | | 128/202.27 |
| 6,874,522 B2 | * | 4/2005 | Anderson | A61M 39/18 |
| | | | | 137/68.3 |
| D558,339 S | * | 12/2007 | Christopher | D24/112 |
| 7,458,615 B2 | | 12/2008 | White et al. | |
| 8,540,698 B2 | * | 9/2013 | Spohn | A61M 5/007 |
| | | | | 604/247 |
| 2006/0096597 A1 | * | 5/2006 | Amann | A61M 16/08 |
| | | | | 128/205.27 |
| 2008/0086087 A1 | * | 4/2008 | Spohn | A61M 5/007 |
| | | | | 604/151 |

* cited by examiner

CONNECTOR FOR MULTIPLE SIZED CONNECTIONS

FIELD OF THE INVENTION

The present invention generally relates to connectors for gas delivery hoses. In particular, the present invention relates to a portion of a connector that facilitates connections between a first conduit and a second conduit. The first connector portion of the connector facilitates connections to two different types and/or sizes of second connector portions.

BACKGROUND OF THE INVENTION

Breathing apparatus are used with interfaces to supply a flow of breathing gases to users. Connectors are used to join the breathing apparatus to the interface. In many applications, the connectors used to join the breathing apparatus to the interface include proprietary connectors such that the interface of one company will not connect to the breathing tube, which is connected to the breathing apparatus, of another company. In some applications, a standard connector can be used on the end of the breathing tube. For this reason, care provides typically stock multiple configurations of interfaces to ensure that the selected interface can be joined to the breathing tube.

SUMMARY OF THE INVENTION

In accordance with certain features, aspects and advantages of the present invention, a connector is formed from a first portion and a second portion. The first portion is sized and configured to mate with at least two different second portions. In this manner, the first portion increases the likelihood that a single interface can be connected to a plurality of breathing tubes (i.e., tubes with proprietary connectors as well as tubes with standardized connectors). In this manner, two separate ranges of interfaces need not be maintained, which reduces the required stock levels for customers using both breathing tubes having differing end connectors. Moreover, such a connector can reduce confusion and customer dissatisfaction. Furthermore, when a user is moved from one type of machine to another, the interface can be connected to each machine with less compatibility concerns because the connector portion on the end of the interface tube is more likely to mate with the connector portion on the end of the breathing tube regardless of the manufacturer of the breathing tube.

Accordingly, in some configurations that are arranged and configured in accordance with certain features, aspects and advantages of the present invention, a male end portion for a gases supply conduit connector is provided. The male end portion comprises a proximal end and a distal end. The proximal end is configured to connect to a conduit and the distal end is configured to mate with two or more different female end portions. The distal end of the male end portion comprises a first male connector and a second male connector. The first male connector generally encircles the second male connector with a radial gap defined between the first male connector and the second male connector. The first male connector comprises an outer wall that extends distally from a proximal end wall. The outer wall is generally cylindrical but tapers along at least a portion of its length such that a proximal portion of the outer wall has a larger outer diameter than a distal portion of the outer wall. The second male connector comprises an inner wall. The inner wall comprises an outer surface. The outer surface of the inner wall is spaced apart from an inner surface of the outer wall to define a gap between the inner wall and the outer wall.

In some configurations, the inner surface of the outer wall is generally cylindrical in shape. In some such configurations, the inner surface of the outer wall of the first male connector includes a stepped portion. In some such configurations, the stepped portion defines a first inner diameter at a proximal end of the inner surface and a second inner diameter at a distal end of the inner surface with the first inner diameter being larger than the second inner diameter such that a recess is defined in the inner surface.

In some configurations, the first male connector extends a first axial distance from the proximal end, the second male connector extends a second axial distance from the proximal end, and the first axial distance and the second axial distance are about equal.

In some configurations, a radiused end is positioned at a junction of the outer wall of the first male connector and the proximal end wall.

In some configurations, the inner wall of the second male connector comprises a generally cylindrical inner surface.

In some configurations, the outer surface of the inner wall also comprises three outerwardly projecting ribs. Each of the ribs extends toward the outer wall only a portion of a distance defined between the outer surface of the inner wall and the inner surface of the outer wall.

In some configurations, the ribs are generally trapezoidal in configuration.

In some configurations, the male end portion is used in combination with a female end portion.

In some configurations, the male end portion is used in combination with an interface tube.

In some configurations, the male end portion is used in combination with an interface.

BRIEF DESCRIPTION OF THE DRAWINGS

These and other features, aspects and advantages of the present invention will now be described with reference to the drawings of a preferred embodiment, which embodiment is intended to illustrate and not to limit the invention, and in which figures.

DETAILED DESCRIPTION OF THE INVENTION

Figure 1:
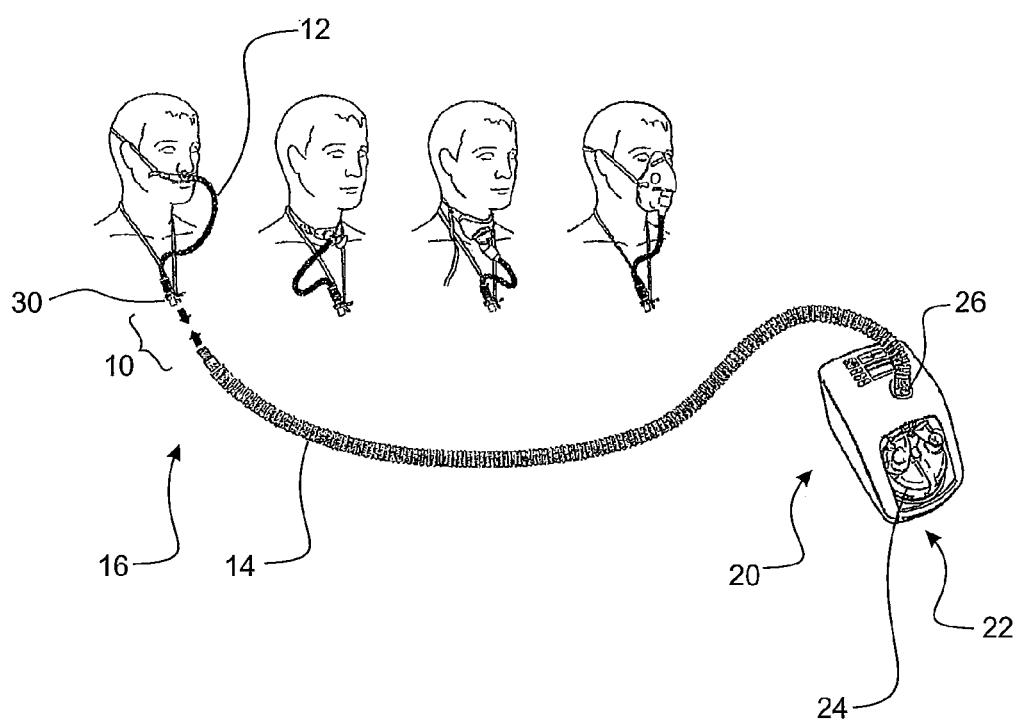
FIG. 1 illustrates a breathing apparatus with which a connector arranged and configured in accordance with certain features, aspects and advantages of the present invention has certain benefits. The apparatus is shown with a variety of interfaces that can use the connector.

With reference initially to FIG. 1, a connector 10 is shown connecting an interface tube 12 to a breathing tube 14. The connector 10 can be used to connect other components in other environments but the present configuration is particularly suitable to breathing assistance apparatus uses and the like. The connector 10 (and any of the related components) can be configured in any suitable manner, including but not limited to that disclosed in U.S. Pat. No. 7,458,615, which is hereby incorporated by reference in its entirety.

The connector 10, together with the interface tube 12 and the breathing tube 14, define a portion of a circuit 16 that can be used to respiratory care or treatment. The circuit 16 receives a flow of pressurized air or other gases from a source 20. The source 20 can be bottled gases, wall gases or a blower, for example but without limitation. The source 20 can delivered heated air or other gases, humidified air or other gases or both heated and humidified air or other gases. In some configurations, such as the illustrated configuration, the source 20 simply supplies a flow of pressurized air or other gases.

A flow properties modification device 22 can be interposed between the source 20 and the breathing tube 14. In some configurations, the flow properties modification device 22 and the source 20 can be combined into a single structure or component. In the illustrated configuration, the flow properties modification device 22 comprises a humidifier.

The humidifier 22 can have any suitable configuration. The illustrated humidifier 22 comprises a humidification chamber 24. The humidification chamber 24 can contain a volume of water that is heated in any suitable manner. In some configurations, the humidification chamber 24 has a plastic body that is connected to a highly heat-conductive base. In some configurations, the base is formed of aluminum. The device 22 also comprises a heater plate (not show) that generates heat that is transferred through the highly heat-conductive base into the water within the humidification chamber 24.

The device 22 comprises an outlet 26 and the breathing tube 14 is connected to the outlet 26. The flow being delivered into the breathing tube 14 through the device 22 and from the source 20 is passed into the interface tube 12, which is joined to the breathing tube 14 with the connector 10. A nasal cannula 28 or any other suitable patient interface can be connected to the interface tube 12 such that the flow delivered into the interface tube 12 can pass through the nasal cannula 28 into the user.

The connector 10 can include a first portion and a second portion that can be fit together in any suitable manner. The first portion can be an interface-side portion 30. The interface-size portion can be secured to the interface or to the interface tube 12 in any suitable manner. In some configurations, the interface-side portion 30 is joined to the interface tube 12 such that removal of the interface-side portion 30 from the interface tube 12 would destroy the usability of the interface tube 12 and, therefore, the interface. In some configurations, as will be described below, the interface-side portion 30 is joined to the distal end of the interface tube 12 with clips or other suitable mechanical couplers.

Figure 2:
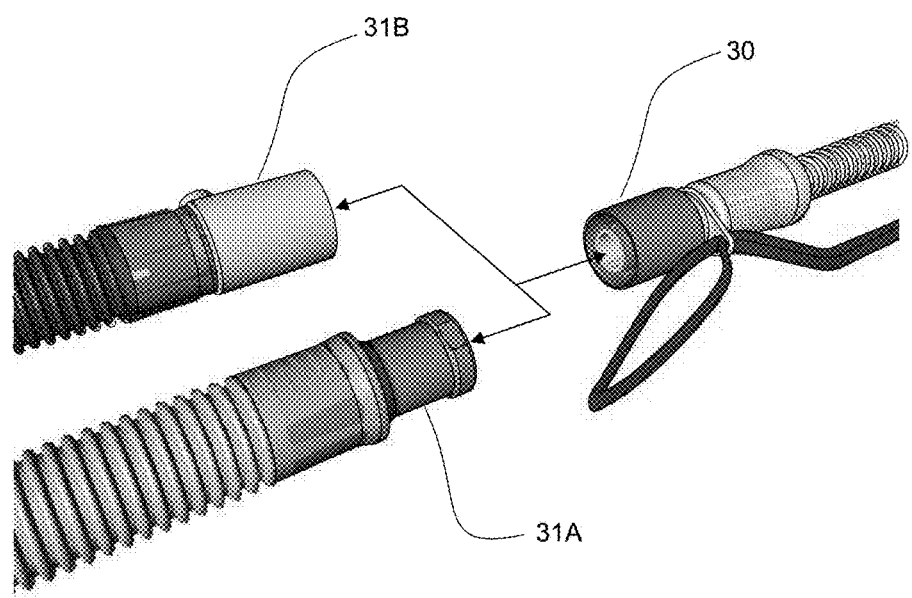
FIG. 2 illustrates the connector of FIG. 1, which has a first portion that is configured to mate with two different second portions.
Figure 2A:
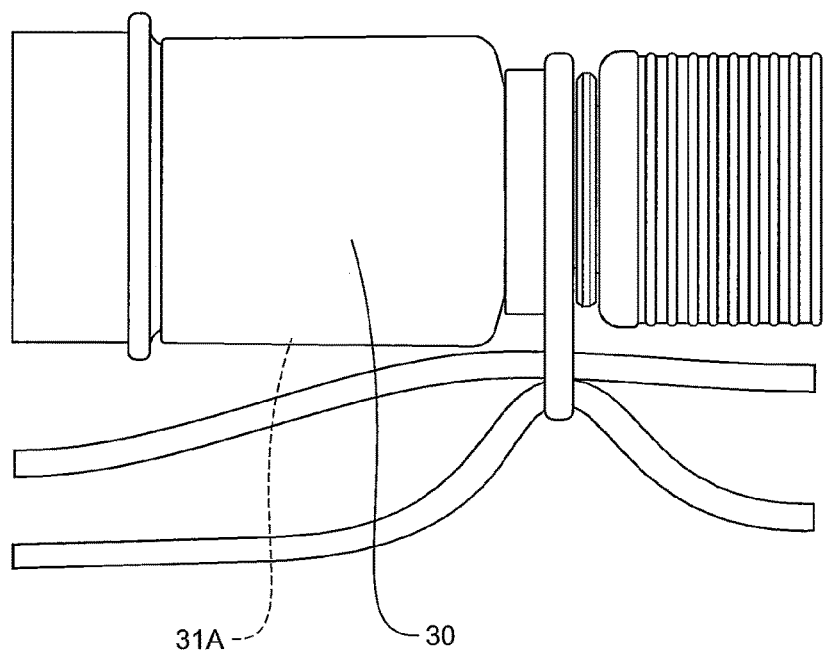
FIG. 2A and FIG. 2B illustrate the connector of FIG. 1 mated with the two different second portions.
Figure 2B:
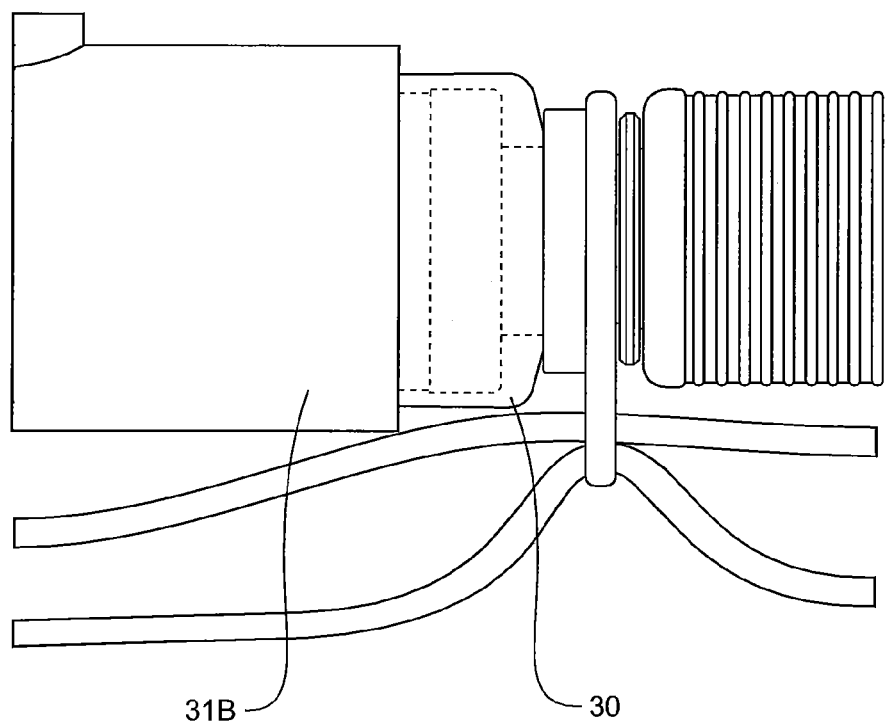

With reference now to FIG. 2, an interface-side end portion 30 of the connector 10 will be described in greater detail. As will be explained, the interface-side end portion 30 of the connector 10 is arranged and configured to facilitate connection to two different source-side end portions 31A, 31B. Connection with each of the two different source-side end portions 31A, 31B is shown in FIGS. 2A and 2B. In some configurations, the interface-side end portion 30 of the connector 10 is arranged and configured to facilitate connection to two different sizes of source-end portions. In some such configurations, the interface-side end portion 30 comprises two distinct male connector portions. In some such configurations, because the connector portion 30 is attached to the end of an interface, a single interface can be used with two different sized source-side end portions 31A, 31B (i.e., the end portions that couple to a breathing tube 14), which advantageously reduces the number of discrete interface models (e.g., cannula models) that need be stocked in different care settings while simultaneously obviating a need for an adaptor or the like. For example but without limitation, the illustrated interface-side end portion 30 is configured: (1) to connect with a proprietary connector 31A on the end of a PT-series breathing circuit (i.e., the connector on the Airvo breathing circuit) or on the end of an RT241 (i.e., the connector on the end of the MR880 breathing circuit) and (2) also to connect with a 22 mm connector 32B on the end of an inspiratory limb of other breathing circuits (e.g., adult RT-series breathing circuits used with the MR850). Other configurations can be used and, in some configurations, the connectors can be switched with the breathing tube connector being capable of connecting to multiple sizes or types of connectors.

Figure 3:
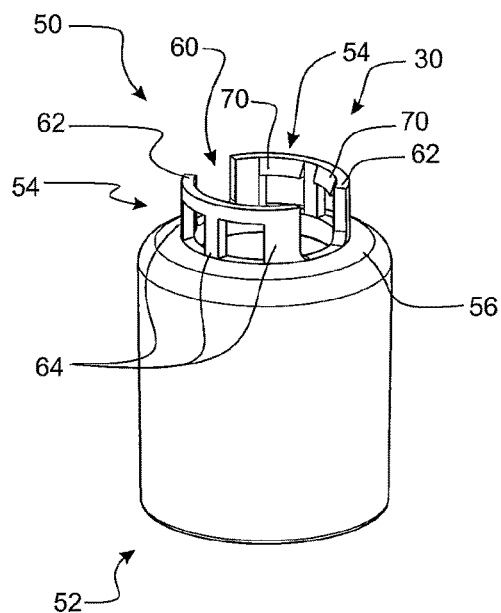
FIG. 3 is a perspective view of the first portion of the connector of FIG. 1.
Figure 4:
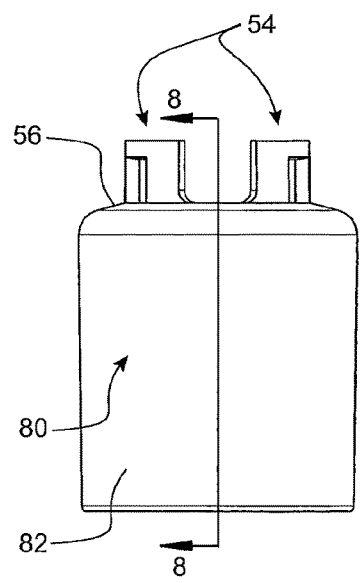
FIG. 4 is a side view of the first portion shown in FIG. 3.
Figure 5:
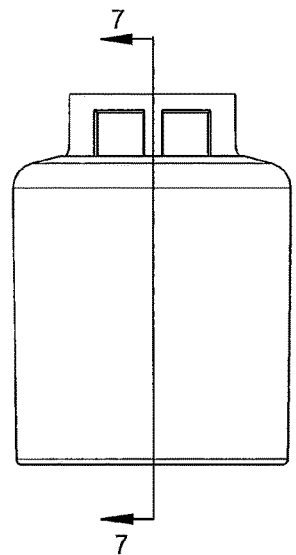
FIG. 5 is a side view of the first portion shown in FIG. 3.

With reference now to FIG. 3, the interface-side end portion 30 will be described in greater detail. As illustrated, the interface-side end 30 comprises a proximal end 50 and a distal end 52. The proximal end 50 connects to the interface tube 12 (i.e., is closest to the interface 28) while the distal end 50 mates with the female source-side end portion of the connector 10 (i.e., is furthest away from the interface 28). The interface-side end portion 30 is generally tubular in shape. Together with the source-side end portion, the interface side end portion 30 forms a connector that allows components in a breathing system to be connected or disconnected from each other easily, thus enabling easy disconnection and reconnection of the patient interface and the source with reduced, or minimal, disturbance to the user or the system.

Figure 7:
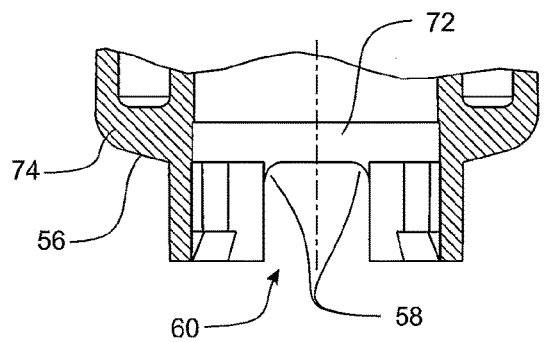
FIG. 7 is an enlarged section through the side view of FIG. 5, taken along the line 7-7.

The proximal end 50 comprises one or more flange 54. While a single flange 54 can be used, two or more flanges 54 are preferred for reasons discussed below. The two or more flanges 54 extend upward from an end surface 56. The two or more flanges 54 define an open ring-like structure at the proximal end 50 of the interface-side end portion 30. At least one gap 60 defines and opening in the one or more flange 54 and at least two gaps 60 separate the two or more flanges 54 that define the ring-like structure. In the illustrated configuration, two gaps 60 divide the ring-like structure into two flanges 54. As illustrated in FIG. 7, the gaps 60 can have generally axially extending edges with rounded lower corners 58 to strengthen the lower portions of the flanges 54. In some configurations, the rounded lower corners 58 can have a radius of between about 0.5 mm and about 1.5 mm. In some configurations, the radius is about 1 mm.

The two or more flanges 54 in the illustrated configuration include a proximal rim 62 that is supported on two or more posts 64. Three posts 64 support the illustrated proximal rim 62. In some configurations, the posts 64 can be spaced apart. The spacing of the posts 64 in the illustrated configuration also defines one or more windows 66. By spacing apart the posts 64, the windows 66 result in reduced material such that the flanges 54 can more easily deflect outward for assembly to the end of the very flexible interface tube 12. In other words, the flanges 54 have increased flexibility, which is desirable due to the flexibility of the interface tube 12.

The illustrated rims 62 include at least one catch 70. In the illustrated configuration, both of the two flanges 62 include two catches 70 such that four catches 70 generally encircle a generally circular passageway into the interface-side end portion 30. In some configurations, the catches 70 are generally aligned with the windows 66. In the illustrated configuration, the catches 70 are positioned between the posts 64 such that each catch 70 overhangs one of the windows 66.

Figure 6:
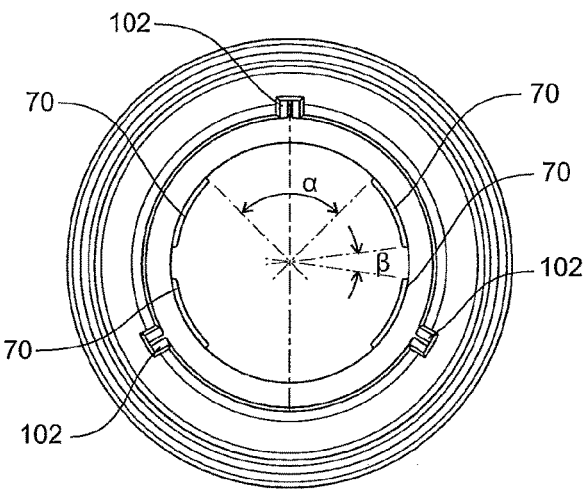
FIG. 6 is a an end view of the first portion shown in FIG. 3.

With reference to FIG. 6, the catches 70 of the two flanges 62 can be separated by an angle α. In some configurations, the angle α can be between about 70 degrees and about 110 degrees. In some configurations, the angle α can be about 90 degrees. By having the angle α be about 90 degrees, the two catches 70 can be positioned within an angle of about 90 degrees as well. Such a configuration accommodates deflection of the flanges 62 while providing generally symmetrical contact between the interface-side end portion 30 and the interface tube 12. The catches 70 of a single flange 54 can be spaced apart by an angle β. In other words, the angle β is defined between the two closest flanges 54 in the illustrated configuration. The angle β can be between about 15 degrees and about 5 degrees. In some configurations, the angle β is about 10 degrees.

The posts 64 are positioned around a perimeter of an opening 72 defined in the end surface 56 of the interface-side end 30. As illustrated in FIG. 7, the end surface 56 can be slightly dome shaped and can taper distally in a radially outward direction. Thus, a region of an end wall 74 proximate the base of the posts 64 is thicker than a radially outward portion of the end wall 74.

Figure 8:
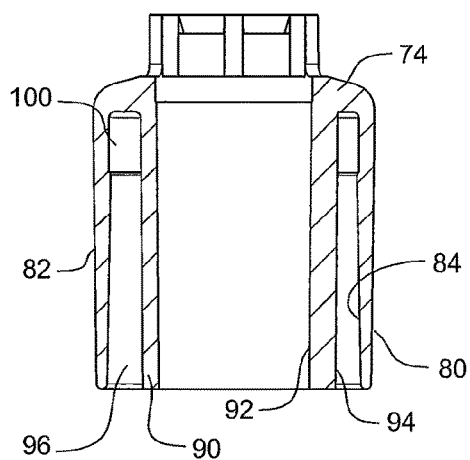
FIG. 8 is a section through the side view of FIG. 4, taken along the line 8-8.

As shown in FIG. 8, an outer wall 80 extends distally from the end wall 74 in the illustrated configuration. For aesthetic reasons as well as removal of any sharp edges, the juncture between the outer wall 80 and the end wall 74 can be radiused. In some configurations, the radius can be between about 3 mm and about 1 mm. In some configurations, the radius is about 2 mm. Between the base of the posts 64 and the most distal portion of the radiused juncture, the end surface 56 tapers between about 1 mm and about 3 mm. In some configurations, the tapering is about 2 mm.

The outer wall 80 preferably defines a tapered, but otherwise generally cylindrical outer surface 82. The tapered outer wall 82 defines a first male connector. In the illustrated configuration, the tapered outer wall 82 defines a 22 mm male conical connector. As such, the tapered outer wall 80 preferably complies with ISO 5356-1, which is hereby incorporated by reference in its entirety. The outer wall 82 defines an outer diameter of about 22 mm+/− 0.03 mm. At the distal end, the outer wall 82 can have an inner surface 84. In some configurations, the inner surface 84 defines an inner diameter of about 20.4 mm. Other inner diameters can be used so long as the outer wall 82 has sufficient strength. The outer surface 82 preferably extends axially a distance of about 22.2 mm.

Figure 9:
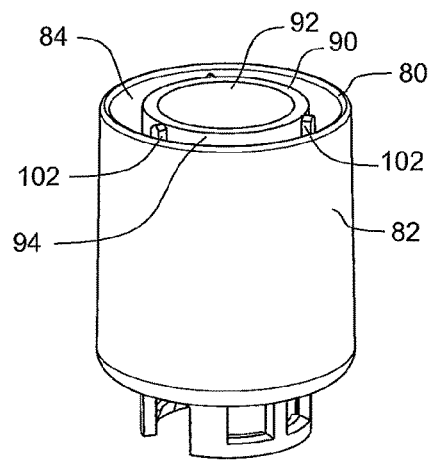
FIG. 9 is a perspective view of the first portion of the connector of FIG. 1.

With reference now to FIGS. 8 and 9, the illustrated interface-side end portion 30 includes a second male connector. In some configurations, the two male connector portions extend the same length and terminate at the same axial distance from the proximal end of the interface-side end portion 30. In some configurations, one of the male connector portions can extend beyond the other in an axial direction.

The second male connector is similar in most regards to the connector shown and described in at least FIG. 11 of U.S. Pat. No. 7,458,615, which patent is hereby incorporated by reference in its entirety. As illustrated, the interface-side end portion 30 comprises an inner wall 90. The inner wall 90 is generally cylindrical and defines a generally cylindrical inner surface 92. In some configurations, the inner wall 90 defines an inner diameter of about 12.05 mm+0.05 mm. Together with the inner surface of the posts 64 and the opening 72, the inner surface 92 defines a passage through the interface-side end portion 30.

The inner wall 90 also has an outer surface 94. The outer surface generally defines an outer diameter. In some configurations, the outer diameter is about 15.4 mm. Thus, a generally annular gap 96 between the outer wall 80 and the inner wall 90 is defined by the inner surface 84 of the outer wall 80 and the outer surface 94 of the inner wall 90. At the distal end, the gap 96 can be about 2.5 mm. Other dimensions are possible. The gap 96 accommodates the source-side end portion in some configurations, as will be described below.

At the proximal end of the gap 96, the inner surface 84 of the outer wall 80 includes a recess 100. The recess 100 is generally annular. The illustrated recess 100 extends about 5 mm in an axial direction. The recess 100 is used to secure the source-side end portion in position when the interface-side end portion 30 is coupled to the source-side end portion as described in U.S. Pat. No. 7,458,615. With the illustrated interface-side end portion 30, however, the outer wall 80 will generally shroud the source-side end portion when the two portions are connected. In addition, with the recess 100 formed in the outer wall 80, the outer wall 80 helps lock the source-side end portion in position when the two portions are connected.

With reference to FIG. 9, the outer surface 94 of the inner wall 90 can include one or more ribs 102. The ribs 102, described as ridges in U.S. Pat. No. 7,458,615, which has been incorporated by reference in its entirety, extend axially (i.e., longitudinally) within the interface-side end portion 30. The ribs 102 will generally align and fit within corresponding recesses formed in the source-side end portion such that the ribs 102 can limit the geometry of the source-side end portions capable of cooperating with the interface-side end portion 30. In the illustrated configuration, the interface-side end portion 30 comprises three ribs 102. The ribs 102 also limit rotation between the interface-side end portion 30 and the corresponding source-side end portion. While the illustrated ribs 102 are generally trapezoidal in configuration, other configurations also can be used.

In use, the interface-side end portion 30 can be alternatively coupled to: (1) a reduced diameter connector that includes recesses to accommodate the ribs 102; or (2) a female medical taper connector. In this manner, when the interface-side end portion 30 is joined to the interface tube 12 that is connected to the interface 28 (e.g., cannula), only a single assembly need be stocked. Prior to the invention of this connector, either multiple assemblies, each having different end connectors, had to be stocked or a set of adaptors would be required. Thus, the connector described above results in a more versatile assembly than previously available.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A male end portion for a gases supply conduit connector, the male end portion comprising:
    a proximal end and a distal end, the proximal end being configured to connect to a conduit, the distal end comprising a first male connector and a second male connector, the first male connector generally encircling the second male connector with a radial gap defined between the first male connector and the second male connector, the first male connector configured to mate with one or more female end portions and the second male connector configured to mate with one or more different female end portions;
    the first male connector comprising an outer wall that extends distally from a proximal end wall, the outer wall being generally cylindrical and having a continuous taper along its length such that a proximal portion of the outer wall has a larger outer diameter than a distal portion of the outer wall, wherein the proximal portion of the outer wall is located adjacent the proximal end wall; and
    the second male connector comprising an inner wall, the inner wall comprising an outer surface, the outer surface of the inner wall being spaced apart from an inner surface of the outer wall to define the gap between the inner wall and the outer wall, wherein the outer surface of the inner wall comprises a plurality of outwardly projecting ribs, each of the ribs extending toward the outer wall only a portion of a distance defined between the outer surface of the inner wall and the inner surface of the outer wall.

2. The male end portion of claim 1, wherein the inner surface of the outer wall is generally cylindrical in shape.

3. The male end portion of claim 2, wherein the inner surface of the outer wall of the first male connector includes a stepped portion.

4. The male end portion of claim 3, wherein the stepped portion defines a first inner diameter at a proximal end of the inner surface and a second inner diameter at a distal end of the inner surface, the first inner diameter being larger than the second inner diameter such that a recess is defined in the inner surface.

5. The male end portion of claim 3, wherein the inner wall of the second male connector comprises a generally cylindrical inner surface.

6. The male end portion of claim 1, wherein the first male connector extends a first axial distance from the proximal end, the second male connector extends a second axial distance from the proximal end, the first axial distance and the second axial distance being about equal.

7. The male end portion of claim 6, wherein a radiused end is positioned at a junction of the outer wall of the first male connector and the proximal end wall.

8. The male end portion of claim 1, wherein the ribs are generally trapezoidal in configuration.

9. The male end portion of claim 8 in combination with a female end portion.

10. The male end portion of claim 8 in combination with an interface tube.

11. The male end portion of claim 8 in combination with a patient interface.

12. The male end portion of claim 11 wherein the patient interface is a nasal cannula.

13. The male end portion of claim 1, wherein an inner surface of the outer wall includes a recess.

14. The male end portion of claim 1, wherein the recess is generally circular.

15. The male end portion of claim 1, wherein the proximal end includes at least one flange configured to allow the proximal end to connect to the conduit.

* * * * *